(12) United States Patent
Arneson

(10) Patent No.: US 6,696,396 B1
(45) Date of Patent: Feb. 24, 2004

(54) THERAPEUTIC SOAP

(76) Inventor: David J. Arneson, 2125 River Beach Dr. Apt. #503, Naples, FL (US) 34104-6960

(*) Notice: Subject to any disclaimer, the term of this patent is extended or adjusted under 35 U.S.C. 154(b) by 0 days.

(21) Appl. No.: 10/316,953

(22) Filed: Dec. 12, 2002

(51) Int. Cl.⁷ ................................................. A61K 7/30
(52) U.S. Cl. ...................... 510/130; 424/54.1; 424/405; 424/406; 424/489; 424/501
(58) Field of Search ........................... 510/130; 424/725, 424/771, 489, 501, 405, 406, 54.1

(56) References Cited

U.S. PATENT DOCUMENTS

| | | |
|---|---|---|
| 4,444,751 A | 4/1984 | Cripps |
| 4,678,668 A | 7/1987 | Darras |
| 5,543,149 A | 8/1996 | Rubin |
| 5,705,166 A * | 1/1998 | Arve ........................... 424/401 |
| 6,419,940 B1 | 7/2002 | Blanton |
| 2002/0192304 A1 * | 12/2002 | Kennedy ..................... 424/725 |
| 2003/0026794 A1 * | 2/2003 | Fein ........................... 424/94.2 |

* cited by examiner

*Primary Examiner*—Necholus Ogden
(74) *Attorney, Agent, or Firm*—C. J. Husar, Esq.

(57) ABSTRACT

A therapeutical soap for treating areas of human skin exposed to insect bites or the venom of marine organisms and poisonous plants contains an enzyme, exfoliating agent and a disinfectant. Use of the soap relieves the itching and swelling resulting from such bites or stings.

7 Claims, No Drawings

THERAPEUTIC SOAP

BACKGROUND OF THE INVENTION

1. Field of the Invention

This invention relates to a novel method of and article for treatment of skin irritation resulting from insect bites or contact with poisonous marine organisms or plants. More particularly, it relates to a new pharmaceutical composition comprising a disinfectant, an exfoliating agent, and an enzyme. It also relates to the article incorporating this composition and the method of its application.

2. Discussion of the Prior Art

Enzymes are known to be used for alleviating insect bites on human skin from mosquitoes and gnats as shown in U.S. Pat. Nos. 4,444,751; 4,678,668; 5,543,149; and 6,419,940. These patents teach the application of a liquid or oil formula to the afflicted skin. Applicant has now discovered a unique composition and a convenient method of treating the irritated skin with a soap of this invention, containing an enzyme that reacts with venom injected into the skin by insects or marine organisms or plants. The composition of this invention furthermore further contains an exfoliating agent to roughen the skin to enable the enzyme to penetrate into the skin surface. The disinfectant soap prevents bacterial invasion.

SUMMARY OF THE INVENTION

The article of the present invention is based on soap as a substrate or carrier and as a disinfectant. Soap, as is known in the prior art, is made by saponification of fats and oils with sodium or potassium hydroxide. The article of this invention further incorporates pumice as an exfoliating agent, and an enzymes such as papain or bromelain, which reacts with the venom injected into the skin and eliminates the source of irritant. The enzyme content is 3–6% by weight and the powdered pumice content is 5–8% by weight. The soap of this invention relieves itch, pain and swelling. The method of treatment of afflicted skin is to apply the composition of this invention to the skin in the presence of water with gentle rubbing motion. A simple application of the soap in accordance with this invention disinfects, exfoliates and neutralizes the venom. It is further found that the soap of this invention is effective in treating the bites of many insects, such as fire ants, sea gnats, bees and wasps. It is also effective in the treatment of venom exposure from jellyfish, fire coral, Portuguese man-of-war and sea lice. In addition, the soap of this invention also is effective against poison ivy and other poisonous plants. The synergistic effect of the soap in disinfecting, exfoliating and neutralizing all in one has not been found in the prior art.

DETAILED DESCRIPTION OF THE INVENTION

As mentioned earlier, the soap is made according to the prior art. The soap of this invention, upon dissolving in water, becomes slightly alkaline which is beneficial in neutralizing the venom and disinfecting the affected skin area. The soap may be hard or soft, solid or liquid, as is known in the prior art. In the process of making the soap, a natural enzyme, such as papain or bromelain is added in the amount of 2–7% by weight, preferably, 3–6% by weight.

The exfoliating agent added is powdered pumice or light-weight shale powder, in the amount of 6–9% by weight, the preferred range being 5–8% by weight.

Optional additional ingredients are vitamin E as a stabilizer and wound healer and beeswax as consistency modifier. FD&C green, or another color may be added to enhance the appearance of the product.

The method of treatment for insect bites on the skin is to first rinse the affected area, gently rub the soap on the affected area for a few minutes to form a layer of suds, and to allow the suds to sit for a few minutes, and then to rinse with clean water and to dry. The process of application of the therapeutic soap may be repeated if necessary.

The embodiment of the invention described here can be modified within the spirit and scope of the present invention. Numerous modifications and variations of the present invention are possible in light of the above teachings.

Having thus described my invention, I claim:

1. A pharmaceutical composition for treating areas of human skin exposed to insect bites or the venom of marine organisms comprising:
   a soap carrier;
   an enzyme selected from the group consisting of papain, bromelain and
   the combination thereof in the amount of 3–6% by weight and
   an exfoliating agent in the amount of 5–8% by weight.

2. The composition of claim 1 wherein the exfoliating agent is powdered pumice.

3. The composition of claim 1 wherein the exfoliating agent is powdered shale.

4. The composition of claim 1 further comprising beeswax as thickening agent.

5. The composition of claim 1 further comprising Vitamin E as stabilizer.

6. A therapeutic soap having the composition of claim 1.

7. A method of treating areas of human skin exposed to insect bites or the venom of marine organisms comprising:
   rubbing said skin with the therapeutic soap of claim 6 in the presence of water for sufficient time to form suds;
   allowing the suds to remain on the skin for 2–3 minutes to react, and by rinsing with water and drying.

* * * * *